United States Patent [19]

Tsuzuki et al.

[11] Patent Number: 5,071,434
[45] Date of Patent: Dec. 10, 1991

[54] BIOLOGICALLY ACTIVE SURFACE CERAMIC AND PROCESS FOR PRODUCING THE SAME

[75] Inventors: Masashi Tsuzuki; Masateru Hattori, both of Aichi, Japan

[73] Assignee: NGK Spark Plug Co., Ltd., Aichi, Japan

[21] Appl. No.: 686,971

[22] Filed: Apr. 18, 1991

[30] Foreign Application Priority Data

Apr. 20, 1990 [JP] Japan .................................. 2-102785

[51] Int. Cl.$^5$ .............................................. A61F 2/28
[52] U.S. Cl. .......................................... 623/16; 501/1; 106/35
[58] Field of Search ................ 505/1; 623/16; 106/35

[56] References Cited

U.S. PATENT DOCUMENTS

| | | | |
|---|---|---|---|
| 4,976,736 | 12/1990 | White et al. ........................... | 623/16 |
| 4,988,362 | 1/1991 | Toriyama et al. ..................... | 623/66 |
| 5,017,518 | 5/1991 | Hirayama et al. ...................... | 501/1 |

*Primary Examiner*—Karl Group
*Assistant Examiner*—Chris Gallo
*Attorney, Agent, or Firm*—Sughrue, Mion, Zinn Macpeak & Seas

[57] ABSTRACT

A biologically active ceramic suitable as a substitute for hard tissues in a living body is disclosed, comprising a dense calcium phosphate ceramic body having formed thereon a surface layer mainly comprising at least one of hydroxyapatite and calcium tertiary $\beta$-phosphate and having a surface roughness of from 10 to 1000 $\mu$m. The surface layer is formed by forming a calcium phosphate coating containing hydroxyapatite and a phosphate or phosphate-containing glass capable of reacting with hydroxyapatite to form calcium tertiary phosphate on a calcium phosphate molded article or a sintered body thereof and calcining the calcium phosphate molded or sintered body with the calcium phosphate coating at a temperature of from 700° to 1350° C. to allow a part or the whole of the hydroxyapatite to react to form calcium tertiary $\beta$-phosphate. The ceramic has improved bioaffinity and sufficient mechanical strength, and can be integrated into hard tissues in a reduced period of time.

5 Claims, No Drawings

BIOLOGICALLY ACTIVE SURFACE CERAMIC AND PROCESS FOR PRODUCING THE SAME

FIELD OF THE INVENTION

This invention relates to ceramics which are widely useful as substitutes for hard tissues in a living body, such as artificial bones, artificial dental roots, and artificial joints, particularly calcium phosphate ceramics with a biologically active surface layer, and to a process for producing the same.

BACKGROUND OF THE INVENTION

Calcium phosphate compounds have affinity for a living body (bioaffinity), and sintered bodies thereof have been studied for use as biological materials capable of substituting for bones or teeth.

Inter alia, hydroxyapatite and calcium tertiary $\beta$-phosphate are excellent in bioaffinity and harmless to a living body and therefore have attracted attention as substitutes for hard tissues in a living body which can be completely integrated into bones through displacement with new bone. A problem associated with these calcium phosphate compounds is that it takes them from 1 to 3 months to have a sufficient bond strength to hard tissue in a living body.

In an attempt to overcome this problem, it has been proposed to use porous calcium phosphate ceramics. However, having considerably reduced strength, such porous ceramics are of little or no use in application to sites or shapes where mechanical strength is needed.

It is considered that high strength zirconia or alumina having thereon a biologically active calcium phosphate coating would be a high strength ceramic material having biological activity. However, since displacement of the calcium phosphate coating with new bone is necessarily followed by appearance of an interface between a zirconia or alumina body and the new bone, integration with a bone cannot be accomplished. Moreover, plasma spray coating or sputtering, which is a currently employed method for forming a calcium phosphate coating, not only incurs high cost, but is incapable of completely controlling a calcium phosphate phase formed.

SUMMARY OF THE INVENTION

Accordingly, an object of the present invention is to provide a calcium phosphate ceramic having practical strength and improved biological activity.

Another object of the present invention is to provide a process for producing such a calcium phosphate ceramic.

The inventors have conducted extensive investigations and reached the present invention as a result.

The present invention is directed to a biologically active surface ceramic which comprises a dense calcium phosphate ceramic body having formed thereon a surface layer mainly at least one of comprising hydroxyapatite and calcium tertiary $\beta$-phosphate and having a surface roughness of from 10 to 1000 $\mu$m.

The present invention also relates to a process for producing the above-described ceramic, which consists of a step in which a calcium phosphate coating containing hydroxyapatite and a phosphate or phosphate-containing glass capable of reacting with hydroxyapatite to form calcium tertiary $\beta$-phosphate is formed on a calcium phosphate molded article or a sintered body thereof, and a step in which the calcium phosphate molded article or sintered body thereof having the calcium phosphate coating thereon is calcined at a temperature of from 700° to 1350° C. to allow reacting a part or the whole of the hydroxyapatite to form calcium tertiary $\beta$-phosphate.

DETAILED DESCRIPTION OF THE INVENTION

The ceramic with a biologically active surface layer according to the present invention is a dense body comprising, as a base material, a ceramic formed of calcium phosphate as a main component. Accordingly, it has sufficient strength for practical use. Further, the ceramic of the present invention has a surface layer mainly comprising at least one of hydroxyapatite and calcium tertiary $\beta$-phosphate and having a surface roughness ($R_z$) of from 10 to 1000 $\mu$m according to JIS B 0601 para. 3.5 (based on ISO R 468). The surface layer is chemically and physically integrated with the inner base material to form a firm and dense body having biological activity. Furthermore, the roughness of the surface layer increases a contact surface area with living tissue to enhance the biological activity. Since both the base material and the surface layer comprise calcium phosphate compounds, the bond strength therebetween is very high.

The ceramic with a biologically active surface layer according to the present invention can easily be produced by a process consisting of forming a calcium phosphate ceramic coating containing hydroxyapatite and a phosphate or phosphate-containing glass capable of reacting with hydroxyapatite to form calcium tertiary $\beta$-phosphate on a calcium phosphate molded article or a sintered body thereof and then calcining the molded article or sintered body with the coating at a temperature of from 700° to 1350° C, to thereby allow a part or the whole of the hydroxyapatite to react to form calcium tertiary $\beta$-phosphate.

In the formation of the calcium phosphate coating, phosphates capable of reacting with hydroxyapatite include magnesium phosphate ($Mg(PO_3)_2$). For example, when a surface layer comprising 90 parts by weight of hydroxyapatite and 10 parts by weight of magnesium phosphate is calcined, most of hydroxyapatite is converted to whitlockite ($\beta$-TCP) having dissolved therein magnesium. As the content of unreacted magnesium phosphate increases, biological activity is believed to be reduced. From experimental experiences, the magnesium phosphate content is preferably limited to 20 parts by weight at the most per 100 parts by weight of the surface layer.

A surface layer having a surface roughness of from 10 to 1000 $\mu$m can be formed by applying a coating material having a predetermined composition to a base material by various methods, such as screen printing, spray coating, and green sheet adhesion, followed by calcination.

Considering the material of the surface layer from the aspect of constituent atom ratio, materials having a Ca/P atomic ratio of from 1.20/1 to 1.80/1 are used. Such materials include a composition prepared by mixing a raw material powder mainly comprising at least one of hydroxyapatite ($Ca_{10}(PO_4)_6(OH)_2$) and calcium tertiary phosphate ($Ca/P=3/2$), or a raw material powder of other calcium phosphate compounds, e.g., calcium pyrophosphate and calcium primary phosphate, with fritted glass consisting mainly of $P_2O_5$—$CaO$ so as to have a composition approximate to hydroxyapatite or calcium tertiary β-phosphate.

Calcination of the coating is carried out at a temperature ranging from 700° to 1350° C. If the calcination temperature exceeds 1350° C., calcium phosphate compounds decompose, failing to form a ceramic surface layer containing hydroxyapatite and calcium tertiary phosphate as main components. If it is less than 700° C., no calcination is achieved.

The thus formed surface layer should have a surface roughness ($R_z$) of from 10 to 1000 μm. A surface roughness of less than 10 μm is insufficient for letting a living tissue in. If it exceeds 1000 μm, the surface layer has reduced strength and easily undergoes fall-off or peeling during handling, failing to retain practical unevenness for letting cells in. A particularly favored roughness of the surface layer is from 50 to 200 μm.

When applied to a deficient part of a hard tissue in a living body as a reinforcement or a filler, the biologically active calcium phosphate ceramic according to the present invention undergoes displacement with new bone and integration into bone through chemical bonding in a short period of time.

The unevenness of the surface of the ceramic not only favors entrance of a living tissue but provides an increased surface area in contact with the living tissue, thereby promoting production of new bone and ensuring rapid and strong bonding between the hard tissue and the ceramic as a reinforcement or a filler in the initial stage of healing. Thus, the time required for fixing the ceramic after operations can be reduced.

Substitute materials to be used in a living body must be stable for a long period of time in agreement with the life of the vital body. From this point of view, since the ceramic according to the present invention is formed of biologically active calcium phosphate compounds from its surface through the inside, it is progressively displaced with new bone and integrated into a bone without being accompanied by any problem.

Incidentally, where calcium phosphate-coated materials which are biologically inactive, e.g., $Al_2O_3$ and Ti, are used as a substitute for hard tissues in a living body, although they exhibit satisfactory sessile to the tissue in the initial stage of healing, there appears an interface between a bone and such a biologically inactive material with the passage of time, resulting in various unfavorable problems such as loosening.

As described above, since the ceramic according to the present invention comprises a mechanically strong calcium phosphate ceramic body having formed thereon an uneven calcium phosphate ceramic layer, it has an increased surface area in contact with living tissue, and thereby produces enhanced biological activity (capability of displacement with new bone).

Further, since new bone is engaged into the unevenness of the surface layer, bonding between the new bone and the ceramic can be accomplished not only by chemical bonding, but also by a physical bonding force. As a result, a higher sessile strength is obtained than with a smooth surface, thereby to accelerate sessile in the initial stage of healing.

The present invention is now illustrated in greater detail with reference to the following Examples, but it should be understood that the present invention is not deemed to be limited thereto. All the percents and ratios are by weight unless otherwise indicated.

EXAMPLE 1

Hydroxyapatite powder was wet blended with 10% of $Mg(PO_3)_2$, and the resulting slurry was spray coated on a calcium phosphate sintered body (hydroxyapatite/calcium phosphate=8/2 in terms of a maximum peak ratio in an X-ray diffraction pattern). The coated body was then calcined at 1150° C. for 2 hours to obtain a ceramic with a biologically active surface layer. In cell culture test the ceramic shows excellent properties in sessile strength and growth rate.

X-ray diffractometry revealed that the surface layer was a calcium tertiary β-phosphate single phase having magnesium dissolved therein. Further, the surface layer had a thickness of about 100 μm having a roughness of from 10 to 50 μm which was attributed to the unevenness formed by spray coating.

EXAMPLE 2

A 1/1 mixed powder of hydroxyapatite and calcium tertiary phosphate was wet blended with 5% of a frit comprising 46 mol% of $P_2O_5$, 3.2 mol% of BaO, 20 mol% of CaO, and 2 mol% of $Al_2O_3$, and the resulting slurry was coated on a sintered body comprising a hydroxyapatite single phase. The coated body was calcined at 1300° C. to obtain a biologically active ceramic. In cell culture test the ceramic shows excellent properties in sessile strength and growth rate.

EXAMPLE 3

Hydroxyapatite was wet blended with 5% of a frit having a Ca/P atomic ratio of 0.6/1, and the resulting slurry was coated with a brush on a calcium phosphate single phase sintered body. The coated body was then calcined at 1200° C. to obtain a biologically active surface ceramic. In cell culture test the ceramic shows excellent properties in sessile strength and growth rate.

EXAMPLE 4

A molded article comprising hydroxyapatite and 5% of a frit having a Ca/P atomic ratio of 0.6/1 was spray coated with a slurry having the same dry composition as the molded article and then calcined at 1200° C. to obtain a biologically active surface ceramic with a roughened surface. In cell culture test the ceramic shows excellent properties in sessile strength and growth rate.

While the invention has been described in detail and with reference to specific examples thereof, it will be apparent to one skilled in the art that various changes and modifications can be made therein without departing from the spirit and scope thereof.

What is claimed is:

1. A biologically active surface ceramic which comprises a dense calcium phosphate ceramic body having formed thereon a surface layer mainly comprising at least one of hydroxyapatite and calcium tertiary β-phosphate and having a surface roughness of from 10 to 1000 μm.

2. A ceramic as in claim 1, wherein said surface layer has a roughness of from 50 to 200 μm.

3. A process for producing a biologically active surface ceramic which consists of a step in which a calcium phosphate coating containing hydroxyapatite and a phosphate or phosphate-containing glass capable of reacting with hydroxyapatite to form calcium tertiary β-phosphate is formed on a calcium phosphate molded article or a sintered body thereof, and a step in which the calcium phosphate molded article or sintered body thereof having the calcium phosphate coating thereon is calcined at a temperature of from 700° to 1350° C. to allow reacting a part or the whole of the hydroxyapatite to form calcium tertiary β-phosphate.

4. A process as claim 3, wherein said phosphate capable of reacting with hydroxyapatite is magnesium phosphate.

5. A process as claim 3, wherein said calcium phosphate coating has a Ca/P atomic ratio of from 1.20/1 to 1.80/1.

* * * * *